US00PP19990P3

(12) United States Plant Patent
Ballington et al.

(10) Patent No.: US PP19,990 P3
(45) Date of Patent: May 12, 2009

(54) BLUEBERRY PLANT NAMED 'NEW HANOVER'

(50) Latin Name: *Vaccinium cormbosum*
Varietal Denomination: New Hanover

(76) Inventors: James Ralph Ballington, 260 Kilgore Hall, Horticultural Science Department, North Carolina State University, Raleigh, NC (US) 27695-7609; Susan Duke Rooks, Horticultural Crops Research Station, 3800 Castle Hayne Rd., Castle Hayne, NC (US) 28429-6519

( * ) Notice: Subject to any disclaimer, the term of this patent is extended or adjusted under 35 U.S.C. 154(b) by 0 days.

(21) Appl. No.: 11/292,375

(22) Filed: Dec. 2, 2005

(65) Prior Publication Data

US 2007/0130659 P1 Jun. 7, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Kent L Bell

(57) ABSTRACT

'New Hanover' is a new and distinct variety of blueberry plant that has the following unique combination of desirable features that are outstanding in a new variety.

1. Early-midseason ripening when prices remain high.
2. Consistent high yields of large size fruit.
3. Very good fruit color, excellent fruit firmness, and very good fruit quality.
4. Fruit with excellent post harvest shelf-life.

3 Drawing Sheets

Latin name of the genus and species: The Latin name of the novel blueberry variety disclosed herein is *Vaccinium corymbosum* Linnaeus.

Variety denomination: The inventive cultivar of *Vaccinium corybosum* disclosed herein has been given the variety denomination 'New Hanover'.

BACKGROUND OF THE INVENTION

The present invention relates to a new and distinct cultivar of *Vaccinium corymbosum* Linnaeus (blueberry) grown as a fruiting woody shrub for commercial agriculture. Blueberries are typically consumed both fresh and in a number of processed products.

The new and distinct variety of blueberry (*Vaccinium corymbosum* Linnaeus) originated from the hand pollinated cross of NC 1522 (unpatented) (female parent)×'O'Neal' (unpatented) (male parent) made in 1981 at the North Carolina State University greenhouses in Raleigh, N.C. 'New Hanover' differed from it's female parent, NC 1522 in plant habit. The plant habit of NC 1522 is low and spreading, while the plant habit of 'New Hanover' is semi-upright.

Seeds from this hand pollination were germinated in winter 1981/1982 in Raleigh, N.C.) and 125 seedlings were established on the Leland L. Barnes, Jr. blueberry farm at White lake, N.C., under a Memorandum of Agreement with North Carolina State University, whereby Mr. Barnes provided the land and care of the plants, and the University retained ownership of the seedlings. When the seedlings reached maturity in 1987, an elite genotype designated as NC 3103 was selected for its superior productivity and fruit size, color, firmness and quality by James R. Ballington and Susan D. Rooks.

During 1988 the original seedling of NC 3103 was propagated by hardwood stem cuttings, and following rooting, single three plant plots were established on North Carolina State University Agricultural Research Service experiment stations located at Castle Hayne and Jackson Springs, N.C., in 1989. Based on its performance in these initial trials, it was propagated again by stem cuttings and established in a replicated trial at the Castle Hayne Research Station in 1996. It was also established in grower observation trials at Hampstead, New Bern and white Lake, N.C. and at the University of Arkansas Research Station at Clarksville, Ark., in 2001 under Memoranda of Agreements with North Carolina State University. Plants of this new variety have remained true to type through these successive cycles of asexual propagation. This new variety has been named the 'New Hanover' cultivar.

SUMMARY OF THE INVENTION

'New Hanover' differs consistently from its 'O'Neal' parent for: dormant one year stem color, red all around vs. red on the exposed side and grayed-orange on the unexposed side; current season stem color, green vs. yellow-green; leaf shape, elliptic to elliptic-obovate vs. narrowly elliptic; and number of flowers per inflorescence, seven vs. five. 'New Hanover' is a new and distinct variety of blueberry with the following unique combination of desirable characteristics outstanding in a new variety. It has very high yield potential, very good fruit quality, and superior fruit size and color similar to the recently released cultivar 'Sampson' (unpatented). It ripens a few days later than 'Sampson' in early midseason and will provide another large size high quality cultivar to follow the latter cultivar in season. Fruit firmness of 'New Hanover' is superior to 'Sampson', and quite superior to the current early midseason industry standard in North Carolina, the cultivar 'Croatan' (unpatented). The fruit has exhibited excellent post harvest shelf-life, superior to 'Sampson' when held in 40° F. storage, and equal to the latter cultivar when held at 50° F. and 70° F. It is also highly successful with propagation by hardwood and softwood stem cuttings. The 'New Hanover' plant is vigorous and semi-upright in habit, the flowers are self-fertile and produce abundant pollen.

BRIEF DESCRIPTION OF THE DRAWINGS

The photographs in the drawings were made using digital photography techniques, and illustrates the colors as true as reasonably possible when using these techniques. Colors in the photographs may differ slightly from the color values cited in the detailed botanical description, which accurately describe the colors of the new *Vaccinium corymbosum* variety. All photographs were taken from plants growing at the Castle Hayne Research Station, Castle Hayne, N.C.

FIG. 1 illustrates the typical plant habit of 'New Hanover'.

FIG. 2 shows the typical flower of 'New Hanover'.

FIG. 3 shows the typical fruit of 'New Hanover'.

DETAILED BOTANICAL DESCRIPTION OF THE VARIETY

The following is a detailed botanical description of a new and distinct variety of *Vaccinium corymbosum* Linnaeus known as 'New Hanover'. The observations below are from mature plants grown in test plots at a standard commercial spacing of 4' between plants in rows and 10' between rows, at Castle Hayne, N.C. Those skilled in the art of cultivar description and evaluation will appreciate that certain characteristics of a variety will vary with older or, conversely, with younger plants. 'New Hanover' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length and cultural conditions. Color notations are based on The Royal Horticultural Society Colour Chart, the Royal Horticultural Society, London, UK, 1995 edition.

For botanical description purposes, 'New Hanover' was compared to its 'O'Neal' parent and to the traditional standard commercial blueberry cultivar in North Carolina, 'Croatan'. The other parent of 'New Hanover', N.C. 1522, is no longer extant. The botanical descriptive data presented are averages of data collected from mature nine year old plants growing in a replicated trial at the Castle Hayne Research Station, Castle Hayne, N.C., in 2005. The exception to using average values was with seed numbers where these were determined from a representative fruit of each cultivar.

Plant:

*Dimensions.*—New Hanover — 1.5 m height, 1.1 m diameter, H/D ratio 1.36. O'Neal — 1.4 m height, 1.1 m diameter, H/D ratio 1.27. Croatan — 1.4 m height, 1.2 m diameter, H/D ratio 1.17.

*Growth habit.*—Semi-upright for New Hanover (FIG. 1), O'Neal and Croatan.

*Vigor.*—Good for New Hanover, O'Neal, and Croatan.

*Mature cane diameter.*—New Hanover — 4.2 cm. O'Neal — 3.5 cm. Croatan — 4.0 cm.

*Mature cane length.*—New Hanover — 1.3 m. O'Neal — 1.1 m. Croatan — 1.2 m.

*Internode length on first flush growth.*—New Hanover — 13.0 cm. O'Neal — 12.0 cm. Croatan — 10.5 cm.

*Number of renewal stems.*—New Hanover — 2.0. O'Neal — 2.5. Croatan — 1.0.

*Dormant mature stem color.*—Gray-brown (RHS 199D) for New Hanover, O'Neal, and Croatan.

*Dormant one year stem color.*—New Hanover — red on both the exposed (RHS 46A) and unexposed (RHS 53A) surfaces. O'Neal — red (RHS 46A) on the exposed surface, grayed-orange (RHS 167C — RHS 168D) on the unexposed surface. Croatan — red (RHS 46A) on the exposed surface, grayed-orange (RHS168D) on the unexposed surface.

*First flush growth stem color in summer.*—New Hanover — green (RHS 138C). O'Neal — yellow-green (RHS 145B). Croatan — yellow-orange (RHS 154C).

*Pubescence on summer and one year dormant stems.*—New Hanover — moderately dense, white, recurved. O'Neal — moderately dense, white, recurved. Croatan — none (glabrous).

Leaves:

*Leaf blade dimensions.*—New Hanover — length 54 mm, width 33 mm, L/W ratio 1.64. O'Neal — length 49 mm, width 24 mm, L/W ratio 2.04. Croatan — length 68 mm, width 28 mm, L/W ratio 2.43.

*Leaf petiole length.*—New Hanover — 3 mm. O'Neal — 4 mm. Croatan — 5 mm.

*Leaf petiole color.*—New Hanover — green (RHS 138C) on both the adaxial and abaxial surfaces. O'Neal — green (RHS 138D) on the adaxial surface, and (RHS 138C) on the abaxial surface. Croatan — green (RHS 138D) on both the adaxial and abaxial surfaces.

*Leaf shape.*—New Hanover — elliptic to elliptic obovate. O'Neal — narrowly elliptic. Croatan — narrowly elliptic to narrowly elliptic-obovate.

*Leaf apex angle.*—New Hanover — acute to acuminate. O'Neal — acute. Croatan — acuminate.

*Leaf base angle.*—Acute for New Hanover, O'Neal, and Croatan.

*Leaf margin.*—Entire for New Hanover, O'Neal, and Croatan.

*Leaf pubescence.*—None for New Hanover, O'Neal, and Croatan.

*Leaf glands.*—None for New Hanover, O'Neal, and Croatan.

*Leaf color.*—The adaxial leaf surface color is green (RHS 137A) and the abaxial surface color also green (RHS 138B) for New Hanover, O'Neal, and Croatan.

Flowers:

*Number of petals.*—Five, fused completely along the margins into a corolla tube so that they cannot be separated for individual petal measurements.

*Number of flowers per inflorescence.*—New Hanover — 7.0. O'Neal — 5.0. Croatan — 8.0.

*Flower dimensions.*—New Hanover — length 9.0 mm, diameter 6.8 mm, L/D ratio 1.3. O'Neal — length 9.0 mm, diameter 7.5 mm, L/D ratio 1.2. Croatan — length 8.0 mm, diameter 5.0 mm, L/D ratio 1.6.

*Length of the single style.*—New Hanover — 7.5 mm. O'Neal — 8.0 mm. Croatan — 8.5 mm.

*Flower shape.*—New Hanover — cylindro-urceolate to urceolate. O'Neal — urceolate. Croatan — cylindraceous.

*Flower color.*—New Hanover — red-purple (RHS 63A) on the fused petal lobes just prior to opening, fading to all white (RHS 155C) on fully open flowers on the outer (abaxial surface if petals were not fused) surface of the fused corolla tube (FIG. 2). White (RHS 155C) on the inner (adaxial surface if petals were not fused) surface of the fused corolla tube. O'Neal — red-purple (RHS 63C) on the basal half of the flowers just prior to opening, fading to all white (RHS 155C) on fully open flowers on the outer surface of the fused corolla tube. White (RHS 155C) on the inner surface of the fused corolla tube. Croatan — red-purple (RHS 62C) on the basal two thirds of the flowers just prior to opening, fading to all white (RHS 155D) on fully open flowers on the outer surface of the fused corolla tube. White (RHS 155D) on the inner surface of the fused corolla tube.

Fruit:

*Fruit dimensions.*—New Hanover — length 14 mm, diameter 20 mm, L/D ratio 0.70. O'Neal — length 15 mm, diameter 19 mm, L/D ratio 0.79. Croatan — length 13 mm, diameter 15 mm, L/D ratio 0.87.

*Fruit shape.*—New Hanover — oblate. O'Neal — oblate. Croatan — round-oblate.

*Fruit pedicel length.*—New Hanover — 5 mm. O'Neal — 5 mm. Croatan — 6 mm.

*Fruit pedicel color.*—New Hanover — upper surface (RHS 49B) red; lower surface (RHS 145B) yellow-green. O'Neal — upper and lower surfaces (RHS 145B) yellow-green. Croatan — upper surface (RHS 51B) red; lower surface (RHS 145C) yellow-green.

*Fruit picking scar.*—New Hanover — 3.0 mm diameter, dry. O'Neal — 1.0 mm diameter, dry. Croatan — 1.0 mm diameter, dry.

*Fruit calyx orientation and prominence.*—Appressed against the apical end of the fruit and not prominent for New Hanover, O'Neal and Croatan.

*Fruit calyx diameter.*—New Hanover — 6–7 mm. O'Neal — 6–7 mm. Croatan — 5–6 mm.

*Fruit color with bloom (epicuticular wax).*—New Hanover — violet-blue (RHS 97C — RHS 97D) (FIG. 3). O'Neal — violet-blue (RHS 97C). Croatan — violet-blue (RHS 97B).

*Fruit color without bloom.*—Black (RHS 202A) for New Hanover, O'Neal and Croatan.

Fruit Sepals:

*Fruit sepal number.*—Five for New Hanover, O'Neal, and Croatan.

*Fruit sepal shape.*—Ovate (triangular) for New Hanover, O'Neal, and Croatan.

*Fruit sepal length.*—New Hanover — 1.1–1.5 mm. O'Neal — 2.0 mm. Croatan — 2.0 mm.

*Fruit sepal width.*—New Hanover — 3–4 mm. O'Neal — 4 mm. Croatan — 3–4 mm.

*Fruit sepal apex.*—New Hanover — acute. O'Neal — acute to acuminate. Croatan — acute.

*Fruit sepal base.*—Fused to (merges with) the skin of the fruit with New Hanover, O'Neal, and Croatan.

*Fruit sepal margin.*—Entire with New Hanover, O'Neal, and Croatan.

*Fruit sepal outer surface color.*—New Hanover — (RHS 97C — RHS 97D) violet-blue. O'Neal — (RHS 97C) violet blue. Croatan — (RHS 97B) violet blue.

*Fruit sepal inner surface color.*—Black (RHS 202A) for New Hanover, O'Neal, and Croatan.

Seeds:

*Number of fully developed seeds per berry.*—New Hanover — 29. O'Neal — 42. Croatan — 28.

*Seed dimensions.*—New Hanover — length 2.0 mm, width 1.0 mm, L/W ratio 2.0. O'Neal — length 1.5 mm, width 1.0 mm, L/W ratio 1.5. Croatan — length 2.0 mm, width 1.0 mm, L/W ratio 2.0.

*Seed shape.*—Basically depressed-ovate for New Hanover, O'Neal and Croatan.

For technical (pomological) description purposes 'New Hanover' was compared to the more recently released blueberry cultivar 'Sampson', along with 'Croatan', at Castle Hayne, N.C. (Tables 2–7), except for time of flowering, where the data was more representative from Jackson Springs, N.C., in 1992 (Table 1). 'O'Neal' was also included in the time of flowering data.

Time of flowering: New Hanover was very similar to O'Neal for dates of first bloom and 50% bloom, although it did start a few days later (Table 1). It was one week earlier than Croatan and Sampson for date of first bloom and 9–10 days earlier than the latter two cultivars for 50% bloom date.

TABLE 1

Time of flowering of blueberry cultivars at Jackson Springs, NC, in 1992.

| Cultivar | Date of first bloom | Date of 50% bloom |
|---|---|---|
| O'Neal | 3/1 | 4/1 |
| New Hanover | 3/5 | 4/1 |
| Sampson | 3/12 | 4/10 |
| Croatan | 3/12 | 4/11 |

Pollination requirements: The flowers of New Hanover are self-fertile.

Pollen production: New Hanover flowers produce abundant pollen.

Season of ripening: With regard to ripening season, New Hanover was a little later than Sampson two years out of three at Castle Hayne, N.C. (Table 2). The first year the plants were three years old and season of ripening often changes with age. It was much later than Croatan two years out of three.

TABLE 2

Season of ripening for blueberry cultivars at Castle Hayne, NC.

| | Cumulative percent ripe by June eighth[1] | | |
|---|---|---|---|
| Cultivar | 1999 | 2000 | 2001 |
| New Hanover | 80 | 54 | 54 |
| Sampson | 43 | 74 | 61 |
| Croatan | 62 | 94 | 82 |

[1]Percent ripe after the first two weeks of the season.

Yield per plant: Yield of New Hanover was excellent, equal to Sampson, and superior to Croatan (Table 3).

TABLE 3

Yield of blueberry cultivars at Castle Hayne, NC.

| | Yield (lbs./plant)[1] | | |
|---|---|---|---|
| Cultivar | 1999 | 2000 | 2001 |
| New Hanover | 9.2 | 19.6a | 21.8a |
| Sampson | 9.0 | 14.5a | 15.8ab |
| Croatan | 7.0 | 6.4b | 10.6bc |

[1]Values not followed by the same letter(s) are significantly different at the 0.05 level (Duncan's Multiple Range Test).

Fruit size (weight per berry): Fruit size of New Hanover was equal to Sampson two years out of three, and superior to Croatan all three years (Table 4).

TABLE 4

Fruit size of blueberry cultivars at Castle Hayne, NC.

| Cultivar | Fruit size (weight per berry in grams)[1] | | | |
|---|---|---|---|---|
| | 1999 | 2000 | 2001 | Average |
| New Hanover | 2.5a | 1.7b | 1.7a | 2.0 |
| Sampson | 2.3a | 2.2a | 1.7a | 2.1 |
| Croatan | 1.6b | 1.5c | 1.3b | 1.4 |

[1]Values not followed by the same letter(s) are significantly different at the 0.05 level (Duncan's Multiple Range Test).

Fruit color: In addition to The Royal Horticultural Society Colour Chart, fruit color was also determined objectively by a Minolta Color Meter (Table 5). The Minolta Color Meter data showed that New Hanover was equal to or superior to Sampson and superior to Croatan. The color meter data showed the same pattern as the colour chart when comparing New Hanover with Croatan, but the differences were greater with the color meter.

TABLE 5

Fruit color and fruit firmness of blueberry cultivars at Castle Hayne, NC.

| Cultivar | Color[1,2] | | Firmness[1,3] | | |
|---|---|---|---|---|---|
| | 2000 | 2001 | 1999 | 2000 | 2001 |
| New Hanover | 19.8a | 19.7ab | 152a | 148a | 185a |
| Sampson | 19.2a | 20.8a | 123b | 125b | 171ab |
| Croatan | 15.8b | 16.7c | 99c | 107c | 151c |

[1]Values not followed by the same letter(s) are significantly different at the 0.05 level (Duncan's Multiple Range Test).
[2]Color (lightness or "L" values) determined objectively by a Minolta Color Meter, Model CR-110, Minolta, Ramsey, NJ. Higher values indicate lighter blue color.
[3]Fruit firmness determined objectively using a Firm-tech Firmness Tester.

Fruit firmness: Fruit firmness determined by a Firm-tech Firmness Tester demonstrated that New Hanover was significantly firmer than Sampson two out of three years (Table 5). It was also firmer than Sampson the third year, but not significantly so. It was significantly firmer than Croatan all three years.

Fruit flavor: Subjective ratings for flavor indicated that New Hanover and Sampson were equal and very good, and that both were superior to Croatan for flavor (Table 6).

TABLE 6

Fruit flavor of blueberry cultivars at Castle Hayne, NC.

| Cultivar | Flavor[1,2] | | |
|---|---|---|---|
| | 1999 | 2000 | 2001 |
| New Hanover | 81a | 79a | 78a |
| Sampson | 79ab | 79a | 78a |
| Croatan | 72c | 74b | 70b |

[1]Values not followed by the same letter(s) are significantly different at the 0.05 level (Duncan's Multiple Range Test).
[2]Subjective ratings based on a 0-90 scale, where less than 60 is unsatisfactory, 60-69 is satisfactory, 70-79 is average to good, and 80 and above superior.

Post harvest shelf-life: Post harvest studies to determine the percent marketable fruit after seven days with fruit held at 40° F., 50° F., and 70° F. demonstrated the superior shelf-life of New Hanover at all three temperatures (Table 7). It was significantly better than Sampson when held at 40° F. for seven days, and equal to the latter cultivar at 50°F. and 70° F. It was significantly better than Croatan at all three post harvest storage temperatures.

TABLE 7

Post harvest shelf-life of the fruit of blueberry cultivars at Castle Hayne, NC, in 2001.

| Cultivar | Percent marketable fruit after seven days[1] | | |
|---|---|---|---|
| | 40° F. | 50° F. | 70° F. |
| New Hanover | 96a | 87a | 45a |
| Sampson | 90b | 83ab | 34ab |
| Croatan | 82c | 77b | 17b |

[1]Values not followed by the same letter(s) are significantly different at the 0.05 level (Duncan's Multiple Range Test).

Propagation: New Hanover is easily propagated asexually by both hardwood and softwood stem cuttings.

Disease reaction: New Hanover has not had any problems with either of the two major diseases affecting blueberries in North Carolina, stem canker (*Botryosphaeria corticis*) and stem blight (*Botryospheria dothidea*).

Herbarium voucher: A voucher of New Hanover will be deposited in the herbarium of North Carolina state university (NCSU) in Raleigh, N.C., USA upon patenting.

That which is claimed is:

1. A new and distinct variety of commercial blueberry plant (*Vaccinium corymbosum* Linnaeus) substantially as illustrated and described, characterized by its early-midseason ripening, high yields, large fruit size, excellent fruit firmness, very good fruit quality and excellent post harvest shelf-life of the fruit.

* * * * *

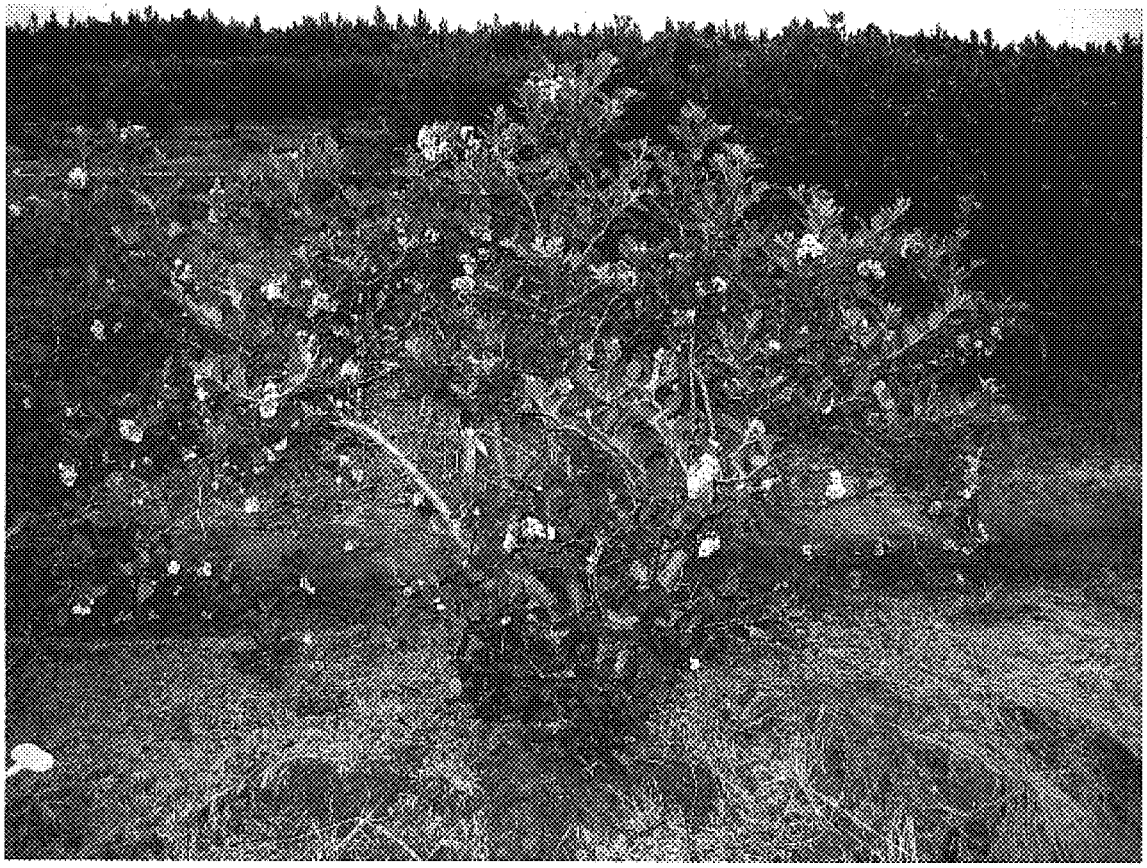
FIGURE 1. NEW HANOVER PLANT HABIT

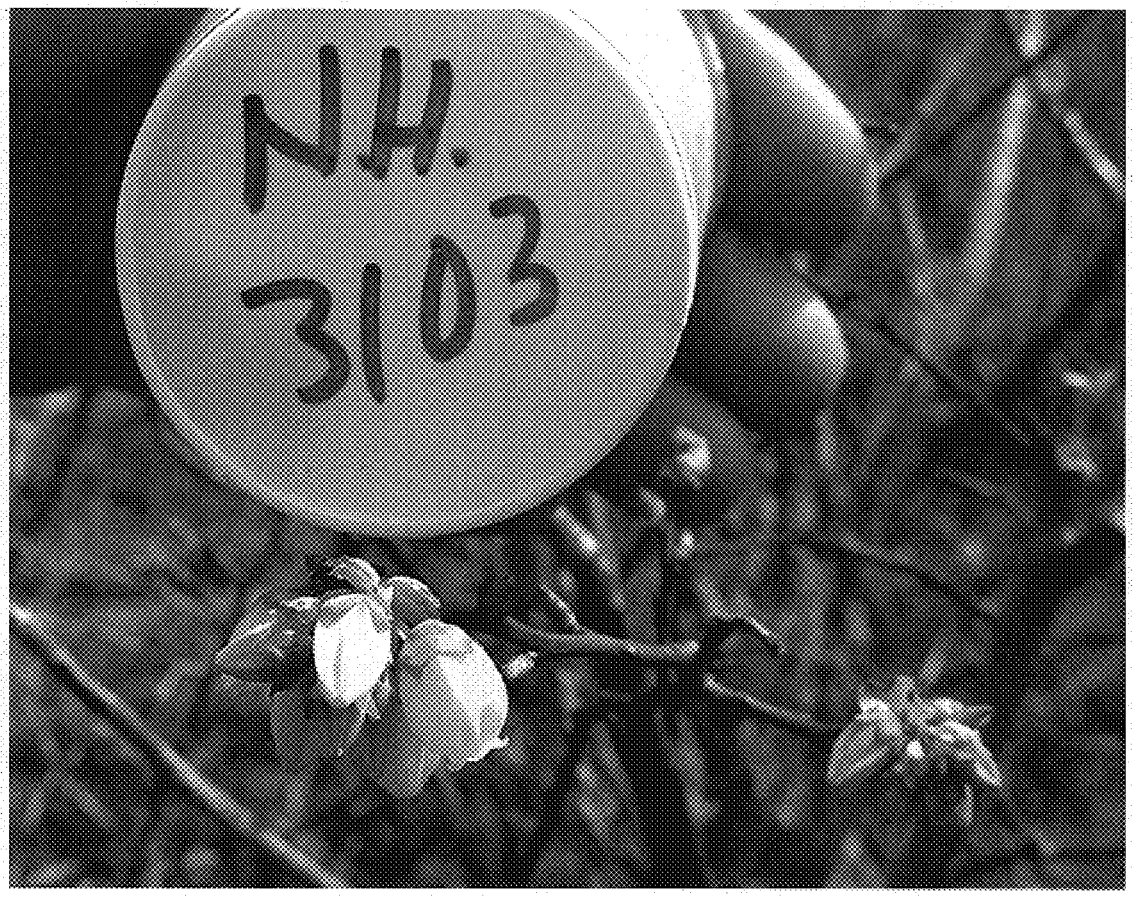
FIGURE 2. NEW HANOVER FLOWERS

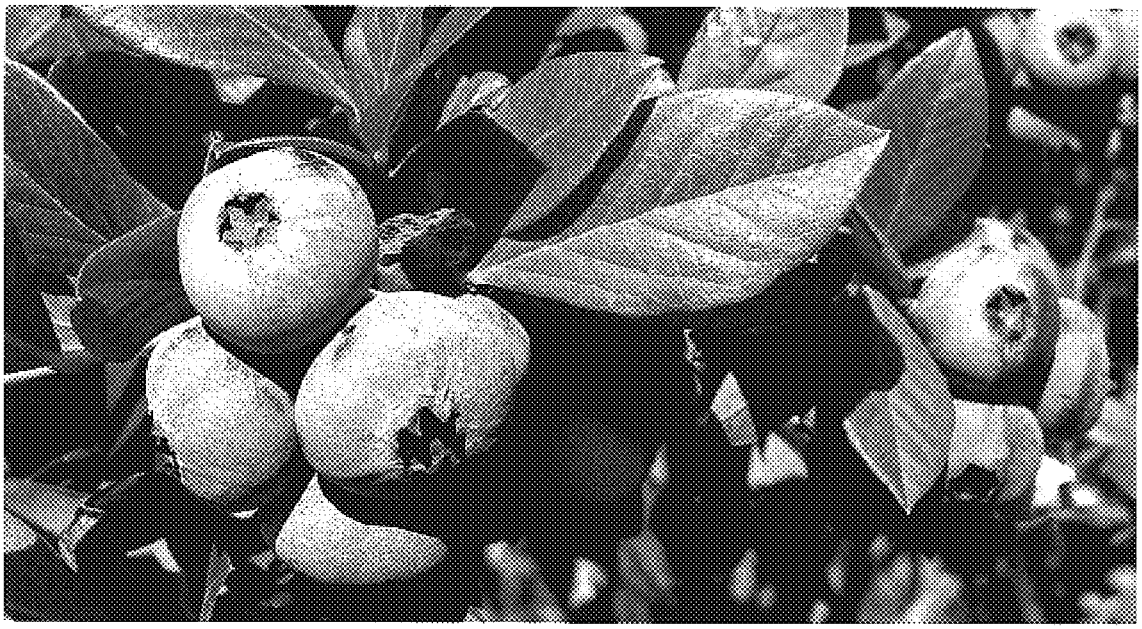
FIGURE 3. NEW HANOVER FRUIT